United States Patent [19]
Neufeld

[11] 4,111,195
[45] Sep. 5, 1978

[54] ORTHOPEDIC UPPER AND LOWER LEG SUPPORT
[76] Inventor: Alonzo J. Neufeld, 1650 Parway Dr., Glendale, Calif. 91206
[21] Appl. No.: 722,869
[22] Filed: Sep. 13, 1976
[51] Int. Cl.² ............................................. A61F 5/04
[52] U.S. Cl. ........................................ 128/83; 128/94
[58] Field of Search .............. 128/94, 87 R, 88, 84 R, 128/84 C, 85, 86, 83, 80 F, 80 R

[56] References Cited
U.S. PATENT DOCUMENTS

| 2,654,365 | 10/1953 | Whitaker | 128/80 F |
| 3,417,748 | 12/1968 | Bimler | 128/88 X |
| 3,762,405 | 10/1973 | DeGeorge | 128/88 X |

FOREIGN PATENT DOCUMENTS

| 35,160 | 11/1905 | Switzerland | 128/88 |
| 36,986 | 7/1906 | Switzerland | 128/88 |
| 73,244 | 9/1913 | Switzerland | 128/88 |

Primary Examiner—John D. Yasko
Attorney, Agent, or Firm—Huebner & Worrel

[57] ABSTRACT

Upper and lower leg supporting apparatus having hinge means articulated so as to be adjustable laterally toward and away from the leg and so as to be movable with the leg in accordance with the bending of the knee.

8 Claims, 8 Drawing Figures

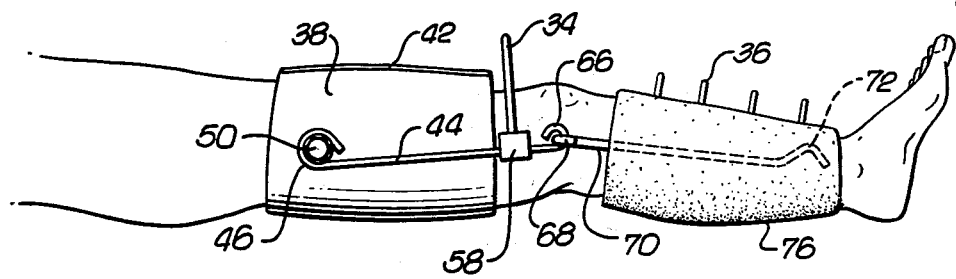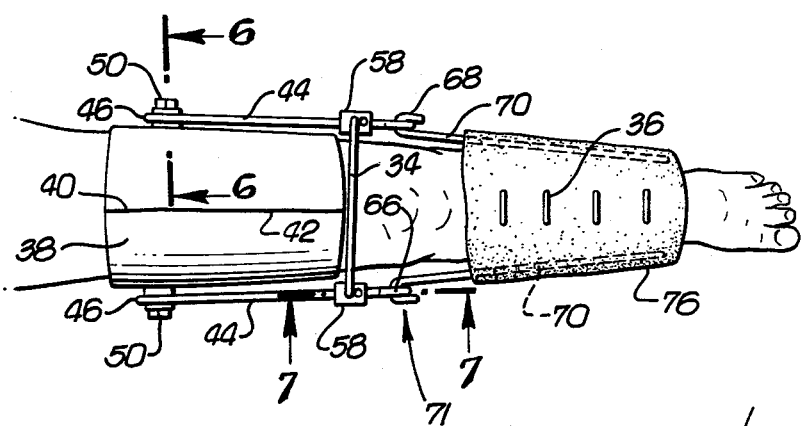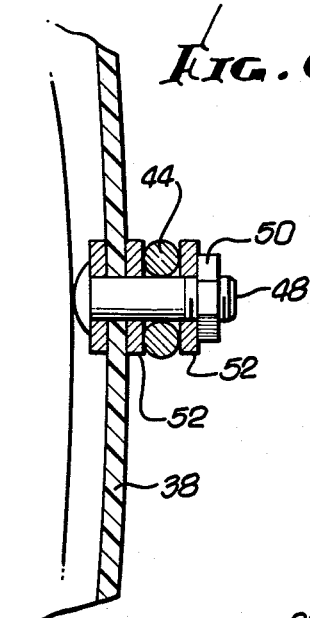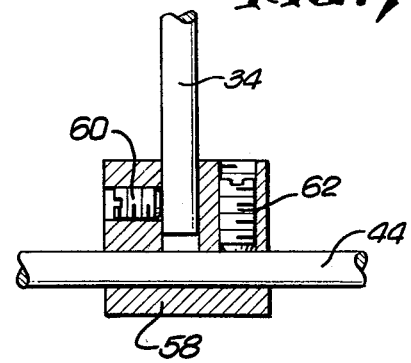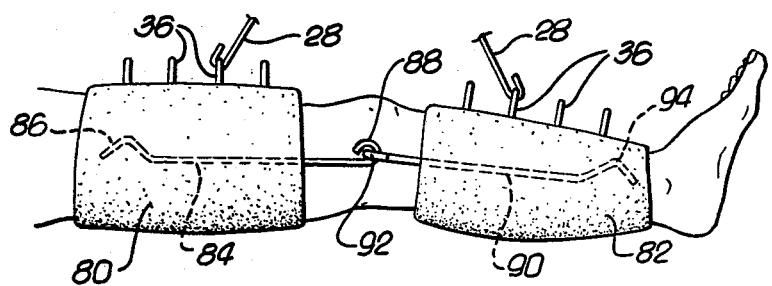

ORTHOPEDIC UPPER AND LOWER LEG SUPPORT

BACKGROUND OF THE INVENTION

Patients having a femur fracture or total implant surgery have their upper and lower legs supported in bed during the healing process. The upper leg is typically enclosed in a relatively loose sleeve and the lower leg is enclosed with a plaster cast. The sleeve and the cast are hinged together to enable the patient to bend the knee to prevent atrophy of the muscles, the hinges being positioned to be actuated in accordance with the bending of the knee. The leg is held upwardly from the bed by a cord having one end connected to the sleeve and the other end connected to the cast. A spring is fitted in the cord adjacent the connection to the cast to permit easy up and down movement of the lower leg, and easy bending of the knee.

One type of prior art hinges has ratchets at the pivot points to permit knee bending but is constructed to not permit lateral movement relative to the leg. This type of hinge provides a severe disadvantage in the cae of patients having a relatively large diameter thigh and a relatively thin calf.

Another type of prior art hinge is made of polypropylene and while it permits lateral movement for fitting on heavy thighs and smaller calves, it is relatively rigid as a hinge and makes it difficult for a patient to bend the knee. The present invention overcomes the disadvantages of the two prior art hinges in that it provides easy fitting on large thighs and small calves, and also permits easy bending of the knee.

SUMMARY OF THE INVENTION

The present invention provides a new orthopedic device having hinges formed of hook and eye connections.

Accordingly, it is an object of the present invention to provide an improved upper and lower leg support apparatus for use on patients having a femur fracture or total implant surgery.

Another object of the invention is to provide improved hinges to permit knee bending for use in apparatus described in the preceding paragraphs.

It is still another object of the invention to provide improved hinges for use with apparatus, described in the preceding paragraphs, and which have adjustable means for positioning the hinges adjacent the upper and lower leg portions. This means also permits variable positioning of the cord connection supporting the upper leg.

It is a further object of the invention to provide hinges for use in apparatus, described in the preceding paragraphs, in which the hinge members connected to the upper leg need not be in straight line alignment with the hinge members connected to the lower leg.

Further objects and advantages of the invention may be brought out in the following part of the specification wherein small details have been described for the competence of disclosure, without intending to limit the scope of the invention which is set forth in the appended claims.

BRIEF DESCRIPTION OF THE DRAWINGS

Referring to the accompanying drawings, which are for illustrative purposes:

FIG. 4 is an enlarged view of the leg supporting apparatus shown in FIG. 1;

FIG. 5 is a plan view of the apparatus, taken along the lines 5—5 in FIG. 4;

FIG. 6 is a fragmentary cross-sectional view, taken along the lines 6—6 in FIG. 5;

FIG. 7 is a cross-sectional view, taken along the lines 7—7 in FIG. 5; and

FIG. 8 is an elevational view of another embodiment of the invention in which the upper and lower leg portions are in plastic casts.

DESCRIPTION OF THE PREFERRED EMBODIMENTS

Figure 1:
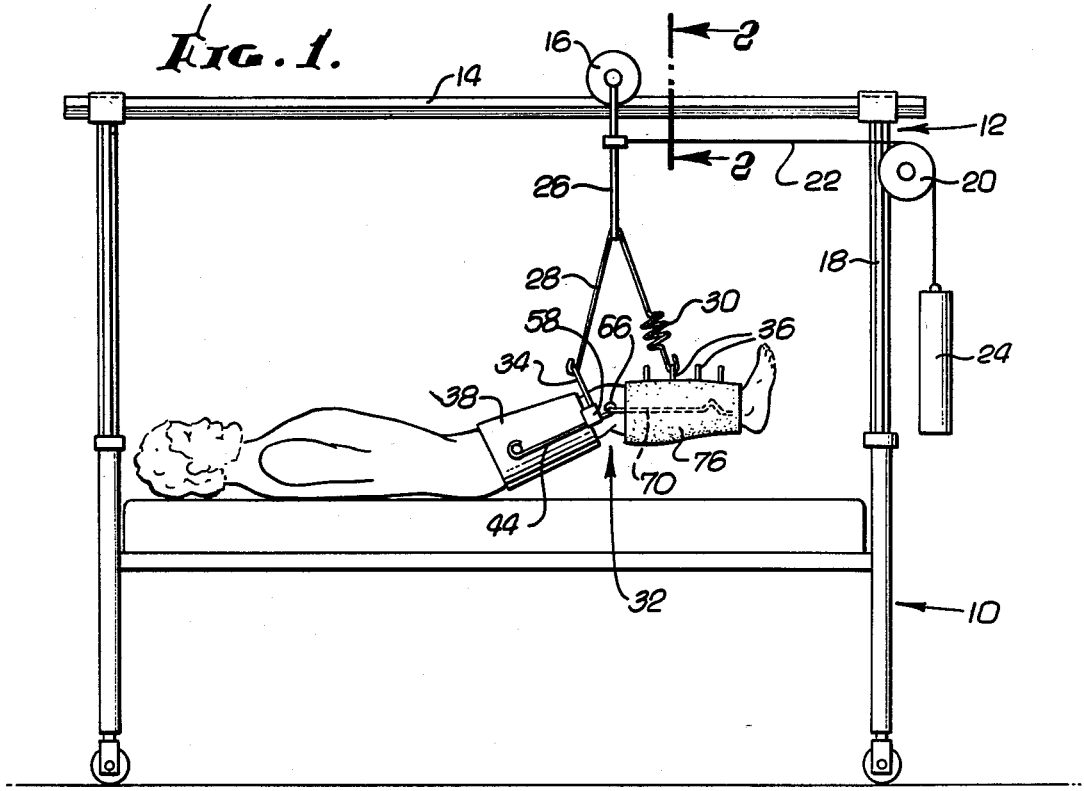
FIG. 1 is a diagrammatic elevational view of the apparatus according to the invention, as used on a patient in bed.
Figure 2:
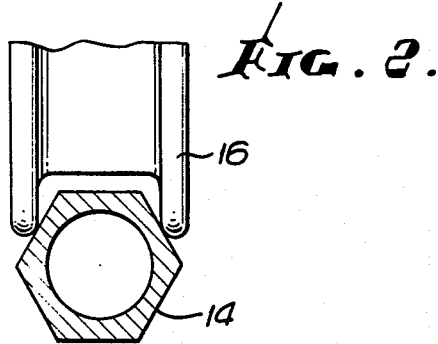
FIG. 2 is a fragmentary view of a roller on a hexagonal rod, taken along the lines 2—2 in FIG. 1.
Figure 3:
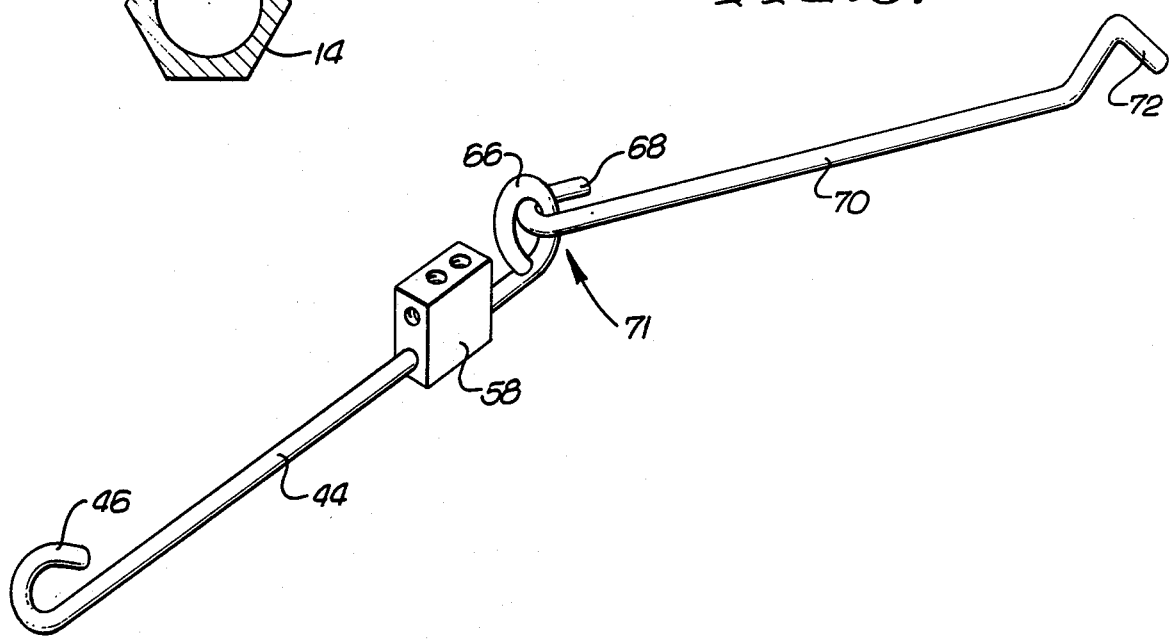
FIG. 3 is a perspective detailed view of a hinge, as shown in the apparatus in FIG. 1.

Referring again to the drawings, there is shown in FIG. 1 a bed rest patient on a bed 10 having an orthopedic frame 12 extending thereabove. A horizontal frame member 14 of hexagon cross section, as shown in FIG. 2, supports a pulley 16 for horizontal movement. Vertical frame member 18 supports a second pulley 20. The pulley 20 has a cord or cable 22 in engagement therewith, a weight 24 being attached to the lower end of the cord. The other end of the cord 22 is attached to a hook 26 supported by the pulley 16. Engaged with the lower end of the hook 26 is a cord 28 having hooks at its ends and having a spring 30 intermediate one of the ends and the hook 26.

The bed rest patient has on one leg an orthopedic upper and lower leg supporting apparatus, generally designated as 32, and which is connected with respect to the upper leg by a loop 34 to the cord 28 and with respect to the lower leg by one of a plurality of loops 36. The thigh or upper leg portion is surrounded by a plastic or canvas sleeve or cuff 38, having a longitudinal cut 40 to permit the sleeve to be opened so as to slip it on the leg. In the position shown, the sleeve 38 is usually relatively loose on the leg but may be tightened or adjusted by means of Velcro fasteners 42, for example. The sleeve 38 is normally securely tightened on the leg for walking.

Laterally outwardly of the sleeve on opposite sides are rods or elongated hinge forming members 44. As shown in FIGS. 3-6, the members 44 have an eye 46 on the outer or upper ends. By means of a bolt 48, nuts 50 and washers 52, the hinge members 44 are tightly secured in a selected position on the sleeve with respect to the leg.

Slidably adjustable on the rods 44 are blocks 58 to which, as best seen in FIG. 7, the ends of the loop 34 are secured therein by means of set screws 60. Longitudinally the blocks are secured be set screws 62 in engagement with the rods 44. The distance between the ends of the loop 34 adjacent the leg is predetermined with respect to the diameter of the thigh so as to position the hinge member 44 laterally with respect to the leg.

At the inner ends of each of the rods 44 are eyes 66 with which are engaged hooks 68 on the inner ends of elongated hinge members or rods 70. The engaged rods 70 and 44 form the hinges, generally designated as 71. The rods 70 have a returning bend 72 at their outer ends to aid in securing the rods in a plaster cast 76 encasing the lower leg. The loop 36 is also encased within the cast.

In a substantial number of patients the thigh of the leg has a considerably larger diameter than the calf so that it is very desirable that the hinge connections be laterally adjustable with respect to the leg outwardly of the knee. This is made possible in the present invention by the hook and eye hinges 71, coupled with the blocks 58 and the loop 34, which serve to properly position the hinge laterally with respect to the leg, in addition to providing a connecting means for supporting the leg upwardly.

In FIG. 8 another embodiment of the invention is illustrated. Here both the upper and lower legs are enclosed in plaster of Paris casts 80 and 82, respectively. On both sides secured within the cast 80 are hinge forming rods 84, each having on its upper end a return bend 86 and on its lower end a hinge eye 88. Similarly, secured within the cast 82 on each side thereof is a hinge forming rod 90, each having on its upper end a hinge hook 92 engaged with a respective hinge eye 88. The lower ends each have a return bend 94.

The upper and lower rods are laterally and vertically positioned in the casts, adjustably spaced from that extending along the leg portions to be easily joined adjacent the knee to form the hinges. Thus, irrespective of the differences of the diameters of the upper and lower leg portions, the rods are easily positioned to extend therealong and be at proper lateral distances therefrom to form hinges that permit easy bending of the knee.

The leg is supported upwardly by a cord 28, as shown in FIG. 1. Each end of the cord is hooked to one of a plurality of loops 36 secured in both of the casts.

The invention and its attendant advantages will be understood from the foregoing description and it will be apparent that various changes may be made in the form, construction and arrangements of the parts of the invention without departing from the spirit and scope thereof or sacrificing its material advantages, the arrangements hereinbefore described being merely by way of example. I do not wish to be restricted to the specific forms shown or uses mentioned except as defined in the accompanying claims, wherein various portions have been separated for clarity of reading and not for emphasis.

I claim:
1. In an orthopedic upper and lower leg supporting apparatus,
an upper leg supporting device,
a lower leg supporting device,
hinge means connecting the devices,
the improvement comprising:
said hinge means being articulated so as to be positionable laterally toward and away from the leg and so as to be at all times easily movable with the leg according to the bending of the knee,
said hinge means including hook and eye connections.
2. The invention according to claim 1 in which:
said hinge means are each formed of two elongated members having distal ends remote from the connections,
the distal end of one of said members being fixed to the upper leg supporting device adjacent its upper end, and
the distal end of the other of said members being fixed to the lower leg supporting device adjacent its lower end.
3. The invention according to claim 1 in which:
said hinge means is comprised of a pair of hinges adapted to move with the knee, one hinge being adapted to be on one side of the leg and the other being adapted to be on the other side of the leg,
each hinge being formed of two elongated members connected at inner ends and having outer ends spaced from the connection, and
in said hook and eye connections one of the members of each hinge having a hook on its inner end and the other having an eye on its inner end, the hook and eye of each hinge being engaged to connect the members to form the hinge.
4. The invention according to claim 3 in which:
the outer ends of the members are fixed to respective upper and lower leg supporting devices,
and means connectible to the members adjacent the upper leg to adjust the hinges in a selected lateral position.
5. The invention according to claim 3 in which:
the outer ends of the members are fixed to respective upper and lower leg supporting devices,
loop connection means on each of the members fixed to said upper leg supporting device,
a loop having one of its ends secured to one of said loop connection means on one side of the leg and having its other end secured to the other of said loop connection means on the other side of the leg.
6. The invention according to claim 5 in which:
said loop connection means are slidably adjustable on said members for positioning said loop along said upper leg.
7. The invention according to claim 6 in which:
said secured ends of said loop are spaced laterally a selected distance to position the hinges laterally with respect to the leg.
8. The invention according to claim 7 in which:
said loop is adapted to extend above said upper leg,
a support line engaging member extending upwardly from said lower leg supporting device,
said loop and said last member being adapted to be secured to a support line by which the leg is supportable upwardly.

* * * * *